United States Patent [19]

Barnet

[11] 4,298,996
[45] Nov. 10, 1981

[54] MAGNETIC RETENTION SYSTEM FOR INTRAOCULAR LENS

[76] Inventor: Ronald W. Barnet, 523 West Vista, Phoenix, Ariz. 85021

[21] Appl. No.: 171,413

[22] Filed: Jul. 23, 1980

[51] Int. Cl.³ .............................. A61F 1/16; A61F 1/24
[52] U.S. Cl. ................................................................ 3/13
[58] Field of Search ........................................... 3/13, 1

[56] References Cited

U.S. PATENT DOCUMENTS

| | | |
|---|---|---|
| 2,637,043 | 5/1953 | Worrell ................................. 3/13 |
| 2,661,480 | 12/1953 | Rosen et al. ......................... 3/13 |
| 3,979,780 | 9/1976 | Boniuk ................................. 3/13 |
| 3,994,027 | 11/1976 | Jensen et al. ........................ 3/13 |
| 3,996,626 | 12/1976 | Richards et al. .................... 3/13 |
| 4,073,015 | 2/1978 | Peyman et al. ...................... 3/13 |
| 4,124,905 | 11/1978 | Clark .................................... 3/13 |
| 4,127,903 | 12/1978 | Schachar ............................. 3/13 |
| 4,174,543 | 11/1979 | Kelman ................................ 3/13 |
| 4,177,526 | 12/1979 | Kuppinger ........................... 3/13 |
| 4,206,518 | 6/1980 | Jardon et al. ........................ 3/13 |

Primary Examiner—Ronald L. Frinks
Attorney, Agent, or Firm—Gregory J. Nelson

[57] ABSTRACT

A lens for implantation in the eye upon removal of the crystalline lens. The lens includes a light focusing body and one or more supports extending from the lens body. Each lens support carries a first magnetic fixation member positionable at one side of the iris. A second cooperable magnetic fixation member is positionable at the opposite side of the iris whereby a trans-iris magnetic retention force is exerted between the members to secure the lens in place without the requirement of sutures or incisions in the iris.

9 Claims, 13 Drawing Figures

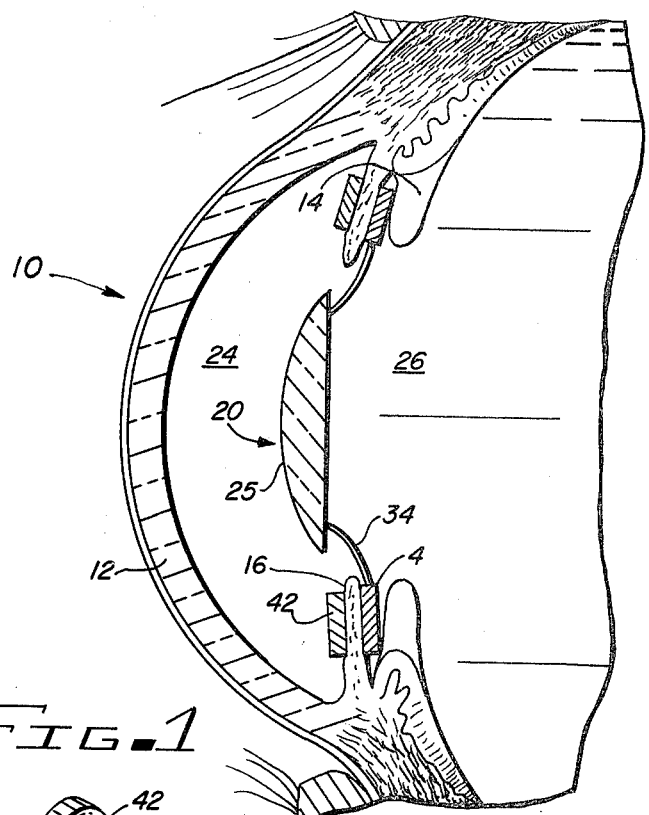
FIG. 1
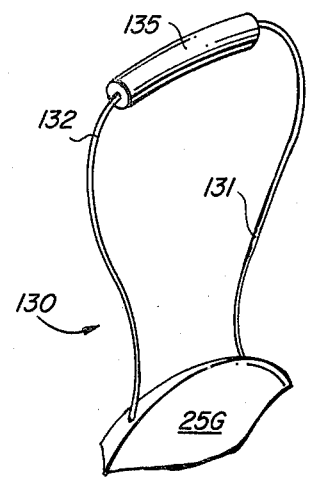
FIG. 13
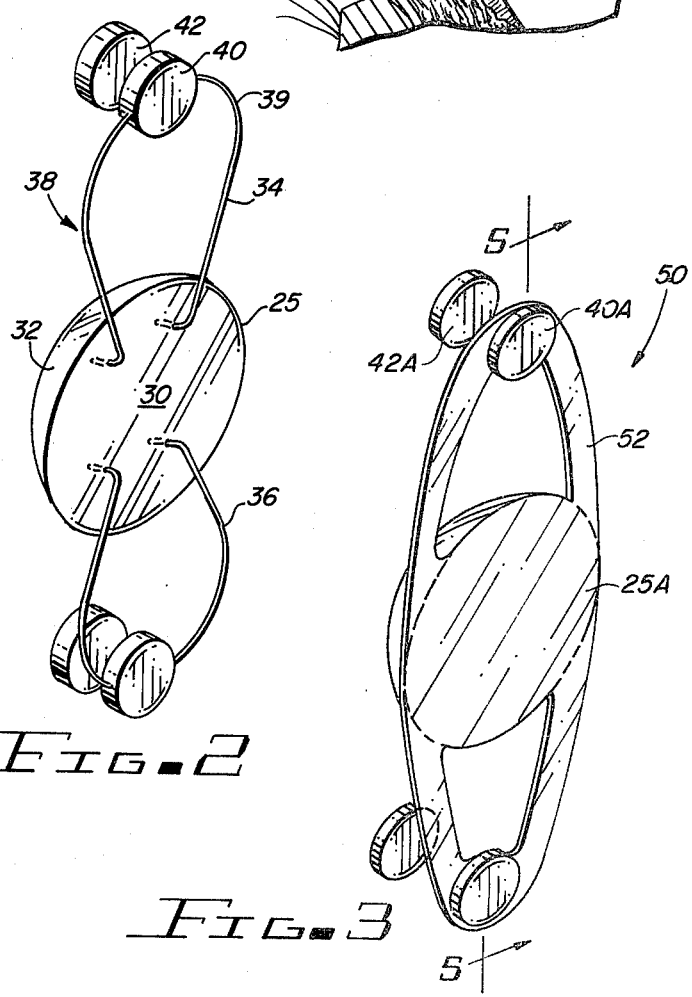
FIG. 2
FIG. 3
FIG. 4

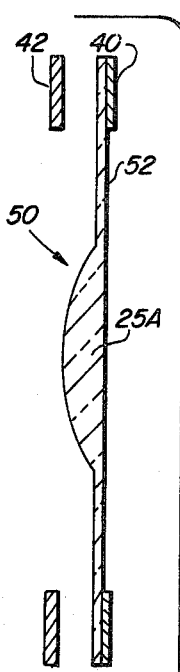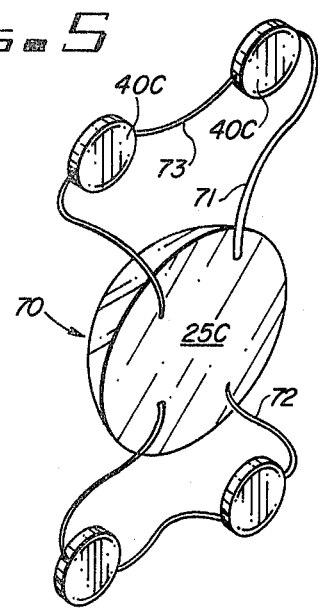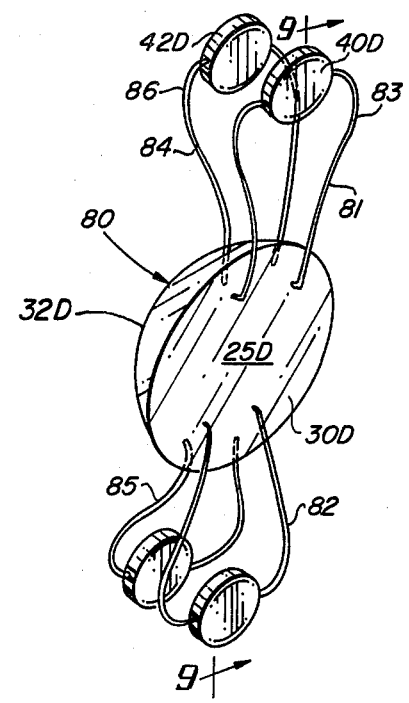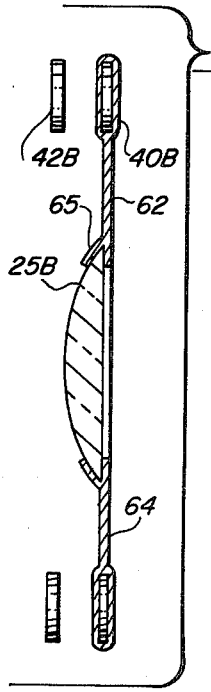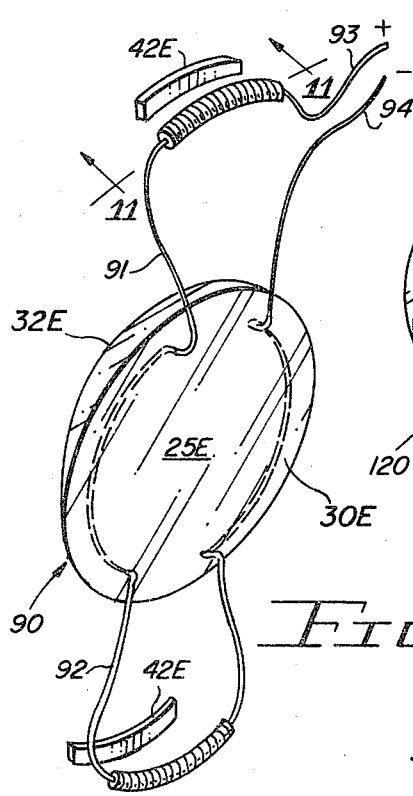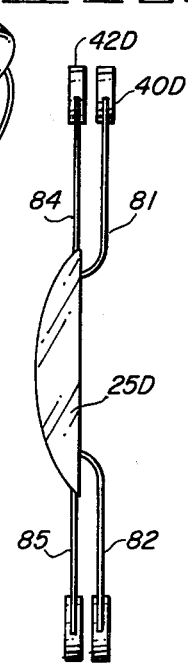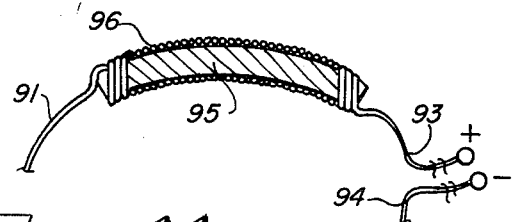

MAGNETIC RETENTION SYSTEM FOR INTRAOCULAR LENS

The present invention relates to intraocular lenses (IOL) for the human eye and more particularly relates to magnetic retention means for securing an IOL in position in the human eye.

The replacement of the crystalline lens portion of the human eye with an artificial intraocular lens implant (IOL) has become an established procedure in the ophthalmolic field. The procedure usually involves a corneo-scleral incision through which the natural crystalline lens is removed and an artificial lens inserted. The inserted lens can be secured in position in either the anterior chamber or the posterior chamber of the eye in accordance with various techniques developed. Intraocular lenses are of various designs and materials and are generally constructed from inert materials such as an optically clear plastic polymeric materials, such as polymethylmethacralate (PMMA), cellulose acetate buterate (CAB) or glass. The lenses have various powers and may be bi-convex, plano-convex or concavo-convex.

Various iris clips and irido-capsular lenses have been developed for securement of these lenses. For example, the lens known as the Binkhorst iris clip lens comprises a plastic lens having four loops which are sutured to the iris. Such suturing is sometimes undesirable in that the sutures may require special surgical techniques and, in some cases, may be torn loose. Lenses of this type may also become dislocated if the eye of the patient is dialated.

Other types of lenses have been developed utilizing only two loops, but such lenses require extracapsular extraction techniques requiring locking of the intraocular lens within the capsule of the crystalline lens.

Other lens mounting arrangements can be found in the prior art. For example, U.S. Pat. No. 4,127,903 to Schachar discloses an IOL with a loop and pin arrangement. Utilizing the loops and pins, the lens may be implanted in a human eye with the pins disposed generally horizontally through apertures in the mid-region of the iris.

U.S. Pat. No. 4,174,543 issued to Kelman shows an intraocular with multiple point position fixation having positioning elements that provide lens stability with respect to the pupil.

Another solution to the problem is found in U.S. Pat. No. 4,124,905, which describes an artificial intraocular lens having posterior and anterior tabs adapted to receive and hold a pin substantially perpendicular thereinbetween. One of the pins is anchored into the lens so that during the surgical implantation the pin cannot be lost.

While the foregoing developments provide certain advantages, a need exists in the art for a system of securing an IOL in position which is effective, stable and which minimizes trauma.

It is an object of the present invention to provide an intraocular lens having a support structure which minimizes the surgical procedure involved in the implantation.

Further, it is an object of the present invention to provide an intraocular lens system which avoids the necessity of a surgical incision through the iris and securing the intraocular lens to the iris with sutures, clips, or pins and which allows the surgeon flexibility in positioning the lens during the procedure.

Further, it is an object of the invention to provide a retention system which adequately secures the lens in place without dislocation particularly during the important initial period immediately after surgery as well as later.

Briefly, the above objects are achieved by the lens of the present invention which includes a medial light focusing lens body with one or more support elements attached to the lens body and extending outward from the lens to an area corresponding to the iris. A first magnetic fixation member is carried on the support member so the fixation member is carried on the support member so the fixation member is positionable at either the anterior or posterior side of the iris. A second magnetic fixation member is positionable opposite the first fixation member on the opposite side of the iris. At least one of the fixation members has magnetic characteristics so a trans-iris magnetic attraction exists therebetween to secure the lens in place.

Other objects and features of the present invention will become more apparent from the following description, claims and drawings in which:

FIG. 1 is a vertical cross-section of an eyeball illustrating a lens according to the present invention implanted therein;

FIG. 2 is a perspective view illustrating an embodiment of the present invention;

FIG. 3 is a perspective view illustrating another embodiment of the present invention;

FIG. 4 is a perspective view illustrating still another embodiment of the present invention;

FIG. 5 is a sectional view taken along lines 5—5 of FIG. 3;

FIG. 6 is a sectional view taken along lines 6—6 of FIG. 4;

FIG. 7 is a perspective view illustrating still another embodiment of the present invention;

FIG. 8 is a perspective view illustrating another embodiment of the present invention;

FIG. 9 is a sectional view taken along lines 9—9 of FIG. 8;

FIG. 10 is a perspective view of another embodiment of the present invention utilizing electromagnetic means;

FIG. 11 is a sectional view taken along lines 11—11 of FIG. 10;

FIG. 12 is a perspective view illustrating yet another embodiment of the present invention; and FIG. 13 is a partial perspective view showing still another aspect of the present invention.

Referring now to the drawings and the various figures therein, particularly FIGS. 1 and 2, reference numeral 10 generally designates an eyeball, portions of which are described herein to facilitate an understanding of the present invention.

Eyeball 10 has a cornea 12 which is part of the external portion of the eyeball. A membrane, not shown, contains cavity 14 and a retina. The natural lens generally occupies a location between the membrane and the iris 16 and is not shown since in implant procedures, this portion of the eye structure is surgically removed prior to implantation of an artificial lens. The artificial lens is generally designated by the numeral 20 and is shown secured to the iris 16, as will be more fully described hereafter. An aqueous zone, between the cornea and the membrane, is divided by the iris into an anterior chamber 24 and a posterior chamber 26. The implant lens 20 has a light focusing portion 25 which may be of polymethylmethacralate (PMMA), cellulose acetate buterate (CAB) or other biologically inert material such as glass. The optical lens 20 is dimensioned to be implanted in the lens region of the eye and may be variously configured and shaped and may be bi-convex, plano-convex, concavo-convex or any other desired shape to correct the wearer's visual deficiency. The particular optical shape of the lens, as pointed out, is designed and selected to provide the correct optical adjustment for the particular patient and the specific shape, size and material of the light focusing lens forms no part of the present invention.

As best seen in FIG. 2, the lens body 25 is shown having a substantially flat posterior surface 30 and a convex anterior surface 32 for purposes of representation. A pair of oppositely disposed haptic support elements 34 and 36 extend from opposite peripheral portions of the lens body 25. The support elements 34 may be constructed from any suitable material, but preferably are polypropylene, platinum, stainless steel or methylmethacrylate or other biologically inert material which is not absorbed by the human body and which will not be rejected by the body. The inner ends of the support members 34 and 36 are secured to the lens by any suitable technique or may be integrally molded as part of the lens.

The support members 34 and 36 consist of a pair of legs 38 extending generally radially from the lens and having their inner ends secured at the posterior surface 30 of the lens, interconnected by a bight portion 39. The length of the support members 34 and 36 may vary, but typically the length of each support member from the peripheral edge of the lens body 25 would be 2-5 millimeters. The support elements 34 are slightly flexible to assist in insertion and placement of the lens. Associated with each of the support elements 34 at a location along the bight 39 is a magnetic retention or fixation element 40. Magnetic element 40 is shown as a substantially flat disc which may be of any suitable magnetic material such as Alnico, bariumferride, silicon iron, or a ceramic material having magnetic properties and may be coated with a nylon or suitable acrylic so the magnetic element is biologically inert. Retention member 42, in the implant position, is oppositely spaced from element 40 disposed on the anterior side of the iris 18. Element 42 is selected so that a trans-iris magnetic attraction exists between elements 40 and 42.

Referring to FIGS. 1 and 2, the implantation technique utilizing lenses of the present invention involves first making standard cataract incision about a portion of the periphery of the cornea. After the incision is made about a portion of the cornea, as for example, 180° or less around the cornea, the cornea is lifted by forceps to expose the iris and the human lens. Mid-iris iridotomies or iridectomies are then performed on opposite sides of the lens at points along a horizontal line cetered at the lens. This involves forming apertures through the iris to facilitate clipping of the intraocular lens. The next step in the technique is the insertion of sutures through the cornea and through the scleral wounds. Alternately, this step may be performed at the conclusion of the surgery. This enables the cornea to be secured after the lens is implanted. The damaged lens is extracted either intracapsularly or extracapsularly. In some procedures the damaged lens may be removed by ultra sonic fragmentation and/or aspiration.

The intraocular lens 20 is then inserted in the concentric area previously occupied by the human lens. The lens is temporarily held in place by forceps, sutures, a temporary guide or similar instrument, with the support elements 34 and 36 engaging or positioned at the posterior side of the iris 14. The magnetic elements 40 engage the iris and elements 42 are positioned on the opposite side of the iris and the magnetic attraction force exerted between elements 40 and 42 across the iris to secure the lens 20 in place. No clips, incisions, or sutures through the iris are required.

The sutures in the cornea are then pulled in order to place the cornea in the normal position. The sutures are tied and air or a chemical subtitute may be introduced into the anterior chamber maintaining the lens a substantial distance from the corneal endothelium. The corneal wound is closed in the conventional manner with sutures. Air is partially removed from the anterior chamber and the anterior chamber is reformed with a balanced salt solution.

With the use of the present lens, magnetic attraction force across the iris is utilized for fixation of the lens and there is minimal chance for dislocation or displacement of the lens. As healing occurs, the magnetic elements 40, 42 remain in place so that they will not later become dislodged.

The present technique does not require suturing of the lens to the iris, thereby eliminating problems with tearing loose of sutures or special implantation techniques.

FIG. 3 illustrates an alternate form of the lens of the present invention generally designated by the numeral 50 again having a light focusing lens body 25A. Throughout the specification the same reference numerals will be used to identify the same or similar elements with an appended letter to distinguish between the various embodiments.

Opposite extending arcuate loops 52 extend from lens body 25A supporting a magnetic element 40A at the bight portion 53 of the loop. Magnetic element 42A and 40A exert a mutual magnetic attraction. Loops 52 may be thin flexible members and may be integrally formed and molded from the same material as the lens body. The embodiment of FIG. 3 is a monoplane structure with intraocular lens suitable for use in either the anterior or the posterior chamber of the eye as best illustrated in FIG. 5.

FIG. 4 illustrates still another embodiment of the present invention generally designated by the numeral 60. Again, the embodiment has a central light focusing body member 25B with a pair of oppositely extended support tabs 62 and 64 supporting magnetic fixation element 40B at the distal end of the tabs. A cooperating magnetic element 42B is adapted to be placed on the opposite side of the iris for securement of the lens. A peripheral flange 65 secures the lens body 25B in place in the support and effectively surrounds the support providing haptic securement. The lens of FIG. 4 again is monoplanar, that is, tabs 62 and 64 are substantially in the same plane as the flat posterior surface of the lens so the lens is adaptable for use in either the anterior or the posterior chamber. The monoplane configuration is illustrated in FIG. 6 and it is noted that magnetic element 40B is encased at the distal end of oppositely extending support tabs 62 and 64. The tabs again may be of any suitable material which is non-toxic, inert and compatible with the human body and the lens as, for example, PMMA or BAC, or the tabs may also be a synthetic such as rayon, which has a surface which will facilitate tissue attachment as healing of the wound at the surgical site progresses.

FIG. 7 illustrates still another embodiment of the present invention generally designated by numeral 70, again having a light focusing lens member 25C from which oppositely extend support loops 71 and 72. Loops 71 and 72 are shown as being generally co-planar with the posterior surface of lens 25C. Loops 71 and 72 are formed having a bight portion 73 which carries a pair of magnetic fixation elements 40C which cooperate with elements, positioned on the opposite side of the iris, not shown.

FIGS. 8 and 9 illustrate still another embodiment generally designated by numeral 80 again having a lens body 25D shown having a convex anterior surface 32D and a substantially planar posterior surface 30D. A pair of support loops 81 and 82 oppositely extend from posterior surface 30D, each supporting magnetic fixation element 40D along the bight portion 83 of the loop. A second pair of loops 84 and 85 oppositely extend from the anterior surface of the lens each supporting a trans-iris magnetic element 42D along the bight portion 86 of the loop. Trans-iris magnetic elements 42D and 40D are spaced apart adapted to be placed on either side of the iris to exert a magnetic attraction therebetween. Support of both of the magnetic elements 40D and 42D on lens attached members further ensures that the magnetic elements will not become dislodged during use by the wearer.

FIGS. 10 and 11 illustrate still another form of the present invention generally designated by numeral 90 and, again, including a central light focusing lens 25E having a substantially flat rear surface 30E and a convex anterior surface 32E. Loop 91 is formed by a conductive wire and extends peripherally along the lens body embedded therein and projecting from the lens to form opposite loop 92. Opposite leads 93 and 94 form part of a continuous electrically conductive path of which loops 91 and 92 are a part. A portion of each of loops 91 and 92 is wound about the winding core 95 forming coil 96 as best seen in FIG. 11. Trans-iris fixation member 42E is adapted to be located opposite winding core 95 so that magnetic attraction is exerted across the iris. When an electromotive force is applied to windings 96 at leads 93 and 94, an electromagnetic force will be generated. Leads 93 and 94 can be temporarily connected to a source of electromagnetic force such as an external battery. When tissue growth has been sufficient to adhere to the windings 96 and to the trans-iris magnetic element 42E, the electrical connection at 93 and 94 can be surgically severed and the lens implant will be secured in place.

FIG. 12 illustrates another embodiment 120 again having a light focusing lens 25F from which oppositely extends support loops 121 and 122. Loop 122 supports a single magnetic member 40F while loop 121 support a pair of magnetic members. This embodiment allows the positioning of the implant lens with a greater fixation force in one area of the iris.

In FIG. 13, embodiment 130 includes lens 25G which carries one or more fixation loops 131 having a bight 132 to which is attached cylindrical magnetic element 135. The cylindrical magnetic element 135 may be preferable in some implants. The shape of the magnetic elements may be variously configured and in some instances may be formed in irregular shapes to fit the geometry of the eye and to provide a better fastening surface for tissue attachment.

As pointed out above, the present lens system does not require suturing the lens to the iris thereby eliminating problems of tearing loose of sutures or require special implantation techniques. The lens of the present invention as has been fully described above, can be made in various configurations and combinations of configurations. Whereas the present invention has been described with respect to specific embodiments, it will be understood that various changes, modifications and alterations will become apparent to those skilled in the art and it is intended to encompass such changes, modifications and alterations as fall within the scope of the appended claims.

I claim:

1. An intraocular lens for implant in the human eye in the anterior or posterior chamber in the area of the iris after removal of the lens, said lens comprising:
   (a) a light focusing lens member having a posterior and an anterior surface;
   (b) a support member extending from said lens to a location corresponding to the iris;
   (c) a first fixation member carried on said support member and adapted to be positioned at one of the anterior or posterior sides of the iris; and
   (d) a second fixation member adapted to be positioned at the opposite side of the iris, at least one of said first and second fixation members having magnetic characteristics whereby a mutual trans-iris magnetic attraction exists therebetween to retain the lens in proper condition.

2. The lens of claim 1 wherein said support member comprises a loop having a bight portion and said first fixation member is secured at said bight.

3. The lens of claim 1 comprising at least a pair of oppositely extending support members.

4. The lens of claim 1 further including second support member extending from said lens and wherein said second fixation member is carried on said second support member.

5. The lens of claim 1 wherein one of said first and second fixation members comprises a generally disc-shaped magnet.

6. The lens of claim 1 wherein at least one of said fixation members comprises electromagnetic means.

7. The lens of claim 1 wherein at least one of said fixation members comprises a permanent magnet shape to facilitate tissue growth attachment.

8. The lens of claim 1 wherein support is biologically inert plastic.

9. The lens of claim 1 wherein support is biologically inert wire loop.

* * * * *